(12) United States Patent
van Hooser et al.

(10) Patent No.: US 7,353,822 B2
(45) Date of Patent: Apr. 8, 2008

(54) CLAMPING ASSEMBLY FOR LIMITING THE DEPTH OF INSERTION OF A RESPIRATORY CARE TREATMENT DEVICE

(75) Inventors: David Theron van Hooser, Fremont, CA (US); Edward B. Madsen, Cumming, GA (US)

(73) Assignee: Kimberly-Clark, Worldwide, Inc., Neenah, WI (US)

( * ) Notice: Subject to any disclaimer, the term of this patent is extended or adjusted under 35 U.S.C. 154(b) by 757 days.

(21) Appl. No.: 10/832,866

(22) Filed: Apr. 27, 2004

(65) Prior Publication Data
US 2005/0235996 A1    Oct. 27, 2005

(51) Int. Cl.
*A61M 16/04* (2006.01)
*A61M 16/08* (2006.01)

(52) U.S. Cl. .......................... 128/202.27; 128/200.26; 128/207.14; 128/912

(58) Field of Classification Search ........... 128/200.24, 128/200.26, 202.27, 203.12, 205.24, 207.14, 128/207.12, 207.15, 207.16, 909, 912; 604/30, 604/33, 35, 246–250, 290, 905, 171, 164.01, 604/164.07, 164.08, 523; 251/280, 142, 251/149, 208, 205, 206, 209, 217, 320, 322; 137/907, 908

See application file for complete search history.

(56) References Cited

U.S. PATENT DOCUMENTS

| | | | |
|---|---|---|---|
| 3,774,616 A | 11/1973 | White et al. | |
| 3,799,173 A | 3/1974 | Kamen | |
| 3,957,055 A | 5/1976 | Linder et al. | |
| 3,991,762 A | 11/1976 | Radford | |
| 4,185,639 A | 1/1980 | Linder | |
| 4,270,529 A | 6/1981 | Muto | |
| 4,327,723 A | 5/1982 | Frankhouser | |
| 4,340,046 A | 7/1982 | Cox | |
| 4,341,210 A | 7/1982 | Elam | |
| 4,502,482 A | 3/1985 | DeLuccia et al. | |
| 4,569,347 A * | 2/1986 | Frisbie ...................... | 606/108 |
| 4,573,965 A | 3/1986 | Russo | |

(Continued)

FOREIGN PATENT DOCUMENTS

EP      1208865 A2    5/2002

(Continued)

*Primary Examiner*—Teena Mitchell
*Assistant Examiner*—Shumay Ali
(74) *Attorney, Agent, or Firm*—James B. Robinson; William W. Letson

(57) ABSTRACT

A medical device clamping assembly includes proximal and distal axially aligned members. The proximal and distal members are movable relative to each other. A channel is defined through the members for receipt of at least a portion of a treatment device therethrough. A clamping member is configured between the proximal and distal members and defines a portion of the channel. The clamping member is actuated between an unclamped configuration and a clamped configuration by moving one of the distal or proximal members relative to the other. In its clamped position, the clamping member clamps upon and restricts axial movement of the treatment device through the assembly; however, the assembling may move on or within the treatment device and does not necessarily limit at least partial retraction of the device from a patient but rather only restricts insertion of the device beyond that point at which the assembly contacts a stopper.

18 Claims, 6 Drawing Sheets

U.S. PATENT DOCUMENTS

| | | | |
|---|---|---|---|
| 4,613,329 A * | 9/1986 | Bodicky | 604/158 |
| 4,825,859 A | 5/1989 | Lambert | |
| 4,838,255 A | 6/1989 | Lambert | |
| 4,863,430 A | 9/1989 | Klyce et al. | |
| 4,902,282 A * | 2/1990 | Bellotti et al. | 604/258 |
| 4,967,743 A | 11/1990 | Lambert | |
| 4,978,341 A | 12/1990 | Niederhauser | |
| 5,060,646 A | 10/1991 | Page | |
| 5,065,754 A | 11/1991 | Jensen | |
| 5,083,561 A | 1/1992 | Russo | |
| 5,097,827 A | 3/1992 | Izumi | |
| 5,107,829 A | 4/1992 | Lambert | |
| 5,133,345 A | 7/1992 | Lambert | |
| 5,135,490 A | 8/1992 | Strickland | |
| 5,139,018 A | 8/1992 | Brodsky et al. | |
| 5,158,553 A | 10/1992 | Berry et al. | |
| 5,158,569 A | 10/1992 | Strickland et al. | |
| 5,163,941 A | 11/1992 | Garth et al. | |
| 5,179,002 A | 1/1993 | Fehder | |
| 5,220,916 A | 6/1993 | Russo | |
| 5,238,218 A | 8/1993 | Mackal | |
| 5,255,676 A | 10/1993 | Russo | |
| 5,277,177 A | 1/1994 | Page et al. | |
| 5,306,272 A * | 4/1994 | Cohen et al. | 606/1 |
| 5,324,271 A | 6/1994 | Abiuso et al. | |
| 5,325,851 A | 7/1994 | Reynolds et al. | |
| 5,338,314 A | 8/1994 | Ryan | |
| 5,360,411 A * | 11/1994 | Mimura et al. | 604/246 |
| 5,431,637 A | 7/1995 | Okada et al. | |
| 5,464,011 A | 11/1995 | Bridge | |
| 5,466,230 A | 11/1995 | Davila | |
| 5,582,161 A | 12/1996 | Kee | |
| 5,605,147 A * | 2/1997 | Truthan | 128/203.12 |
| 5,642,726 A | 7/1997 | Owens et al. | |
| 5,672,179 A | 9/1997 | Garth et al. | |
| 5,676,136 A | 10/1997 | Russo | |
| 5,688,234 A * | 11/1997 | Frisbie | 604/22 |
| 5,720,282 A | 2/1998 | Wright | |
| 5,735,271 A * | 4/1998 | Lorenzen et al. | 128/207.16 |
| 5,749,357 A | 5/1998 | Linder | |
| 5,775,325 A | 7/1998 | Russo | |
| 5,819,727 A | 10/1998 | Linder | |
| 5,842,466 A | 12/1998 | Selman | |
| 5,848,997 A * | 12/1998 | Erskine et al. | 604/533 |
| 5,895,376 A | 4/1999 | Schwartz et al. | |
| 5,935,112 A | 8/1999 | Stevens et al. | |
| 6,086,529 A | 7/2000 | Arndt | |
| 6,109,259 A | 8/2000 | Fitzgerald | |
| 6,109,264 A | 8/2000 | Sauer | |
| 6,165,168 A | 12/2000 | Russo | |
| 6,221,057 B1 | 4/2001 | Schwartz et al. | |
| 6,287,280 B1 * | 9/2001 | Lampropoulos et al. | 604/167.03 |
| D450,837 S | 11/2001 | Cise et al. | |
| D450,838 S | 11/2001 | Cise et al. | |
| D451,194 S | 11/2001 | Cise et al. | |
| 6,331,176 B1 | 12/2001 | Becker et al. | |
| 6,688,306 B1 | 2/2004 | Cise et al. | |
| 6,702,789 B1 | 3/2004 | Owens et al. | |
| 6,729,326 B1 | 5/2004 | Winterton et al. | |
| 2003/0009128 A1 | 1/2003 | Ackerman et al. | |

FOREIGN PATENT DOCUMENTS

| | | |
|---|---|---|
| WO | WO 99/11314 | 3/1999 |

* cited by examiner

CLAMPING ASSEMBLY FOR LIMITING THE DEPTH OF INSERTION OF A RESPIRATORY CARE TREATMENT DEVICE

BACKGROUND

Proper long-term respiratory care of intubated patients requires that multiple medical procedures be performed on the patient. Such procedures may include, for example, ventilation of the patient's lungs; aspiration of secretions from the lungs; oxygenation of the lungs; elimination or reduction of residual $CO_2$ from the lungs; visual inspection of portions of the respiratory system; sampling sputum and gases; sensing parameters such as flow rates, pressure, and temperature of gases within the respiratory system; and/or the administration of medication, gases, and/or lavage.

In the majority of these procedures, a medical treatment device, such as a catheter assembly, is connected to a patient's artificial airway, for example a tracheostomy tube or endotracheal tube. A connecting member, such as an adapter, manifold or other like member, may be attached to the proximal end of the artificial airway and the medical treatment device is inserted through the adapter or manifold and into the artificial airway. The manifold may include a variety of ports through which any manner of medical treatment device may be inserted into the patient's respiratory system for carrying out any combination of the procedures mentioned above.

During certain procedures, it is important that the medical treatment device be precisely positioned in the patient's respiratory system. For example, when using a gas insulation catheter to oxygenate a patient's lungs, it is necessary to precisely position the catheter at the carina of the lung and maintain the catheter in that position. Similarly, it may be necessary to precisely place a biopsy device, sampling device, or monitoring device into the patient's respiratory system and maintain the positioning of the device for the duration of the procedure. However, many of these procedures must be repeated multiple times a day on the same patient and/or require multiple insertions of the device into the patient. Each time an insertion occurs the risk of damaging the patient's respiratory system is present, generally as a result of overinsertion of the device into the patient. This is particularly the case when the insertions are performed by different clinicians such as nurses on different shifts in a hospital.

One concern with current medical devices is that even though many are used for multiple insertions within the same patient there has not been a way to minimize or reduce the risk to the patient upon insertions thereof and especially on the second or subsequent insertions thereof. The present invention provides a reliable and relatively easy to use clamping assembly for limiting the distal advancement or depth of insertion of a medical treatment device into or through a patient's artificial airway and/or respiratory system.

SUMMARY OF THE INVENTION

As used herein, the phrase "artificial airway" includes devices such as tracheostomy tubes, endotracheal tubes, and the like, that define an artificial ventilation path into a patient's respiratory system. The present invention is not limited to use with any particular type of artificial airway.

The present invention is directed generally to a respiratory care assembly particularly suited for use with a ventilating system. In particular, the invention relates to a unique clamping assembly. The clamping assembly provides the clinician with a reliable and effective assembly for limiting the distal advancement or depth of insertion of a medical treatment device through an artificial airway and into a patient's respiratory system. The clamping assembly holds the medical treatment device and limits the depth of insertion of the device into the artificial airway and/or respiratory system of the patient; however, the assembly does allow at least partial retraction of the medical treatment device while the clamp is in use. Complete removal of the medical treatment device may be accomplished by releasing the device from the clamping assembly or disconnection of the device in which the clamping assembly is located from the artificial airway of the patient.

The clamping assembly includes first and second axially aligned members. These members may be considered as "proximal" and "distal" members depending upon their orientation in the respiratory system. At least one of the first and second members is movable relative to the other respective member. In at least one aspect of the invention, at least one of the members is at least partially rotatable. A channel is defined through the first and second members and is configured for receipt of at least a portion of a medical treatment device.

A clamping member is disposed in-line with the first and second axially aligned members. The clamping member defines at least a section or portion of the channel through which at least a portion of the medical treatment device passes. The clamping member has an unclamped configuration wherein the treatment device is slidable through the channel, and a clamping configuration wherein the clamping member clamps upon and restricts axial movement of the medical treatment device through the channel. The clamping member may be operably connected to each of the first and second members so that movement between the members actuates the clamping device.

The first and second members may be threadedly engaged such that threaded rotation of at least one member results in relative axial displacement between the members. In an embodiment, the clamping member may be a compressible annular sleeve member having opposite axial ends that are in contact with the first and second members, respectively. A treatment device, such as a catheter tube, passes through the annular sleeve member. The annular sleeve member may be disposed in a restraining recess such that upon relative axial movement of the first and second members, the annular sleeve is compressed axially. Because the sleeve is restrained in a fixed diameter recess, radial expansion of the sleeve resulting from its axial compression is directed radially inward resulting in reduction of the inner diameter of the annular sleeve thereby causing the sleeve to clamp upon the treatment device disposed therethrough. Once the clamping member is in a clamped configuration the medical treatment device is only slidable in a distal direction until a first end of the clamping assembly, including an extension thereon or therefrom, contacts a stopping or blocking member. To release the treatment device, the clinician simply moves the first and second members in the opposite direction. For example, if the first and second members are threadedly engaged, the clinician rotates a movable member in the opposite direction to release the treatment device.

To aid the clinician in operation of the clamping assembly, it may be desired to incorporate a gripping member on the movable or rotatable member. The gripping member may be, for example, a grip ring having a plurality of grip enhancing protrusions, or the like. The grip ring may define a maximum outer diameter of the respective proximal or distal member.

In one aspect of the clamping assembly, the proximal member is the movable member and the distal member is held stationary. It should be appreciated that this is but one working embodiment. It is just as feasible for the distal member to be rotatable or movable, or for both members to be independently rotatable or movable.

It should also be appreciated that the clamping member need not necessarily be actuated by rotational or axial movement between the proximal and distal members. For example, it is within the level of those skilled in the art to configure a clamping member that operates with a pure rotational or twisting motion as well as a clamping member which operates with pure axial movement. The axially compressible annular sleeve discussed herein is but one aspect of a clamping member that works particularly well with threaded axial displacement between the first and second members. The present invention is not, however, limited to a compressible annular sleeve clamping member.

It should be appreciated that the clamping assembly according to the invention is not limited in its application or use with any particular medical treatment device. The clamping sleeve and axial channels defined through the first and second members may be sized and configured to accommodate any manner of conduit, tube, sleeve or the like, depending on the medical procedure and appropriate medical device. In this description, the medical device is a catheter assembly having a catheter tube that is slidable through the clamping assembly. It should be appreciated that this is merely one aspect of the invention and is presented for purposes of explaining the invention.

The present invention is also drawn to any manner of a respiratory care assembly incorporating the novel clamping assembly described herein. A respiratory care assembly according to the invention utilizes the clamping assembly to introduce any manner of medical treatment device, such as a catheter assembly, through a patient's artificial airway and/or respiratory system. The particular type of medical treatment device is dictated by the desired medical procedure. For example, in a procedure wherein it is desired to aspirate secretions from a patient's lungs, the respiratory care assembly may include a suction catheter assembly incorporating a clamping assembly of the present invention. The suction catheter assembly may include a catheter tube that is slidable through the axial channel defined in the clamping assembly and through the patient's artificial airway to a desired position or location in the respiratory tract for suctioning secretions from the patient's lungs. Once the catheter has been properly placed by the clinician, it is a relatively simple procedure for the clinician to rotate or move a member of the clamping assembly to securely lock the catheter tube in its axial position relative to the clamping assembly so as to restrict distal movement or advancement of the tube beyond the point or depth corresponding to the position at which the clamping assembly contacts the blocking or stopping member.

In another example, the clamping assembly may be independent of the medical treatment device as manufactured. That is, rather than be incorporated into the medical treatment device or medical treatment device assembly, the clamping assembly may be an independent or free standing component.

The present invention is also directed to a method for limiting the depth of insertion or distal advancement of a medical treatment device. The method generally includes providing a clamping assembly having at least a clamped configuration and an unclamped configuration; providing a medical treatment device, at least a portion thereof being configured to pass through the clamping assembly; sliding at least a portion of the medical treatment device through the clamping assembly; and operating the clamping assembly such that axial movement of the medical treatment device relative to the clamping assembly is restricted.

It should thus be appreciated that the invention is not limited to any particular type of medical treatment device or medical procedure, but is useful in any application wherein it is desired to limit or restrict the distal advancement or depth of insertion of a medical treatment device beyond a desired position within the patient's artificial airway and/or respiratory system.

The invention will be explained in further detail below with reference to a particular aspect illustrated in the figures.

DETAILED DESCRIPTION OF THE PREFERRED EMBODIMENTS

Figure 1:
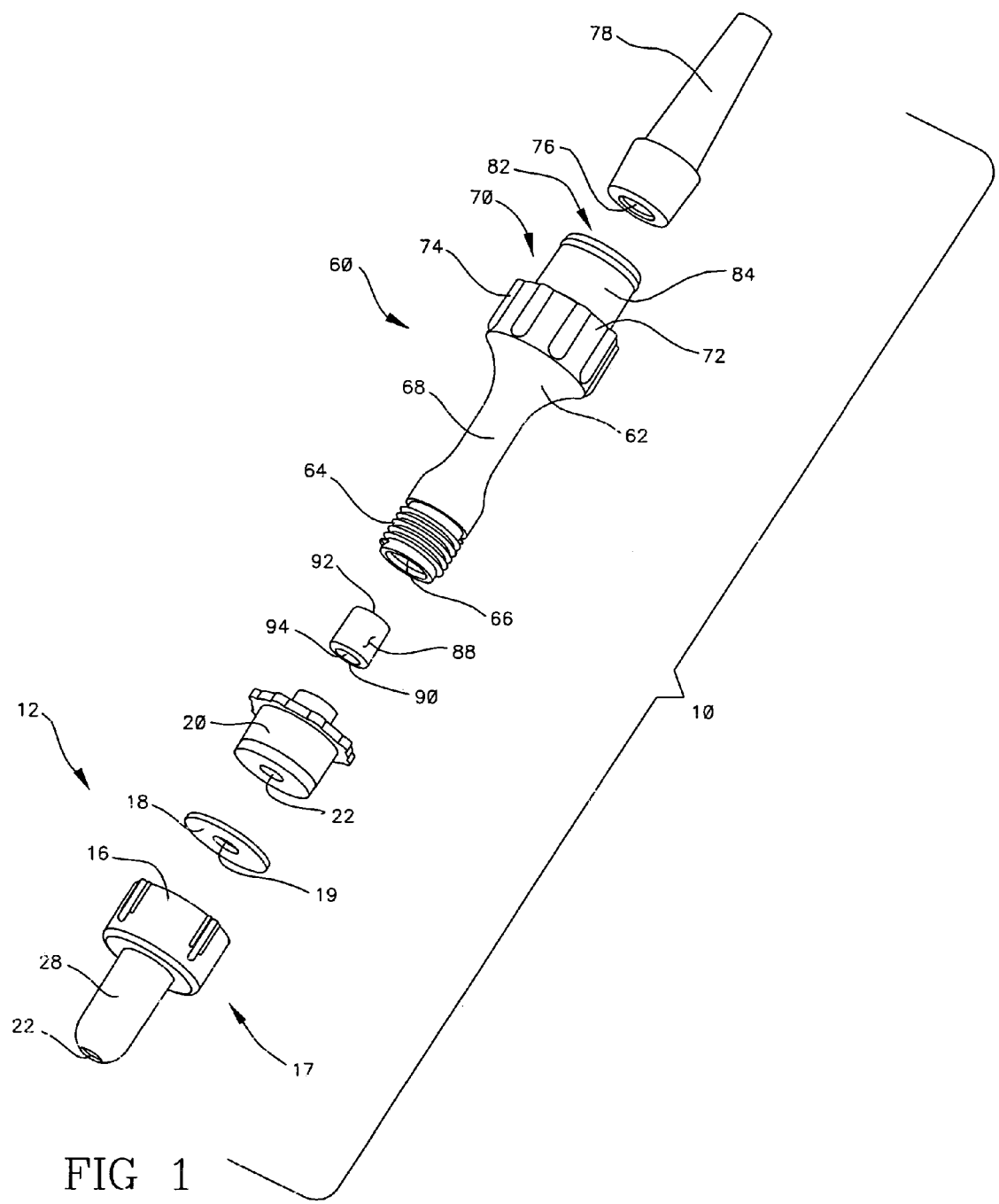
FIG. 1 is an exploded component view of an aspect of the clamping assembly according to the present invention.

Reference will now be made in detail to examples and aspects of the invention. Each example is provided by way of explanation of the invention, and not meant as a limitation of the invention. For example, features illustrated or described as part of one aspect can be used with another aspect to yield a still further aspect. It is intended that the present invention include such modifications and variations not particularly described herein.

In the drawings, each aspect is arranged such that the distal direction (referring generally to the direction closer to the patient or the end of the device which is intended to be closer to the patient in use) is located at the bottom of the figure while the proximal direction (generally referring to the direction closer to the clinician or the end of the device which is intended to be closer to the clinician in use) is located at the top of the figure. However, it will be appreciated that in some aspects it may be possible to invert the orientation of the clamping assembly.

Figure 5:
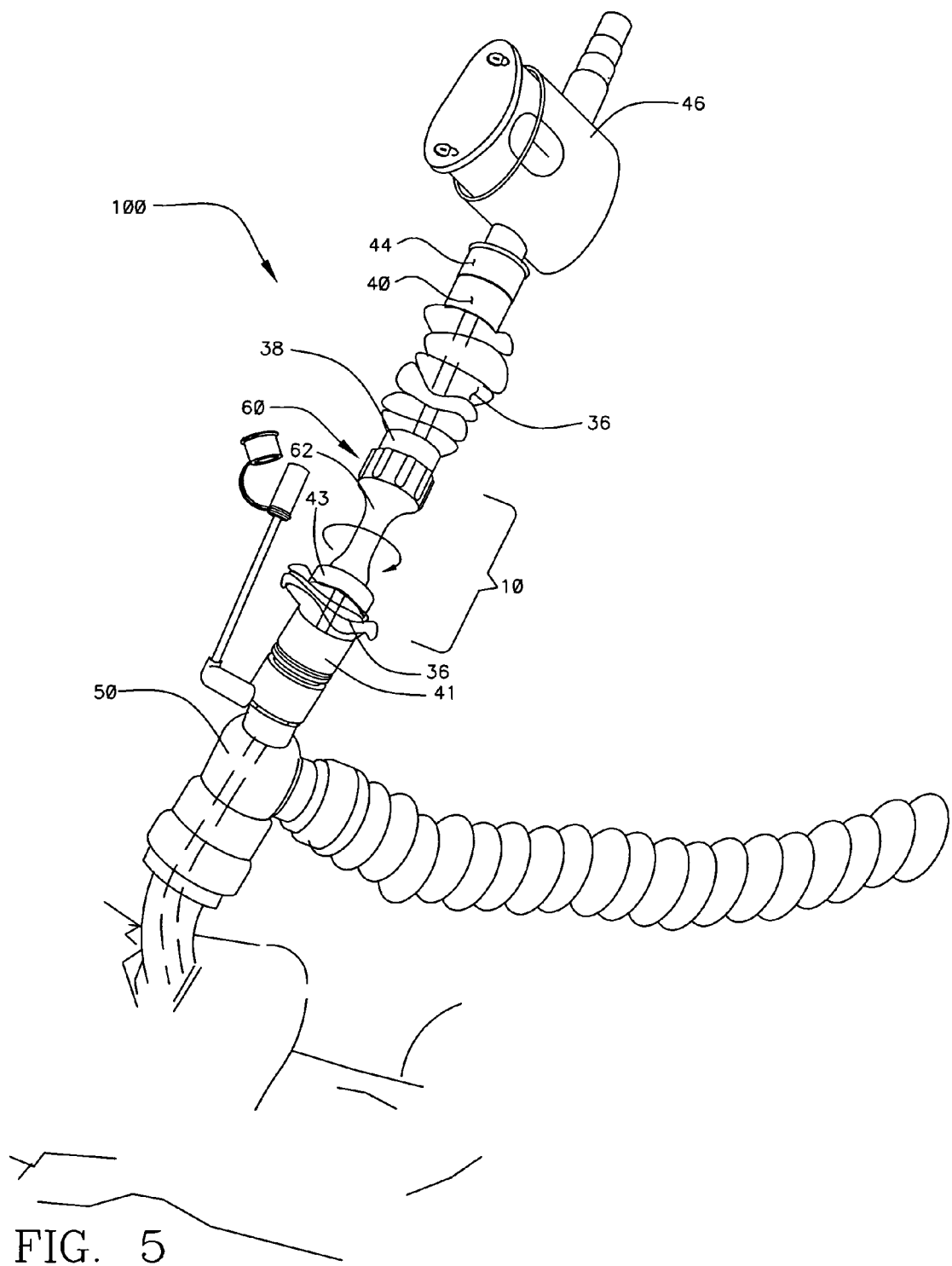
FIG. 5 is a perspective view of a respiratory care assembly according to the present invention.
Figure 6:
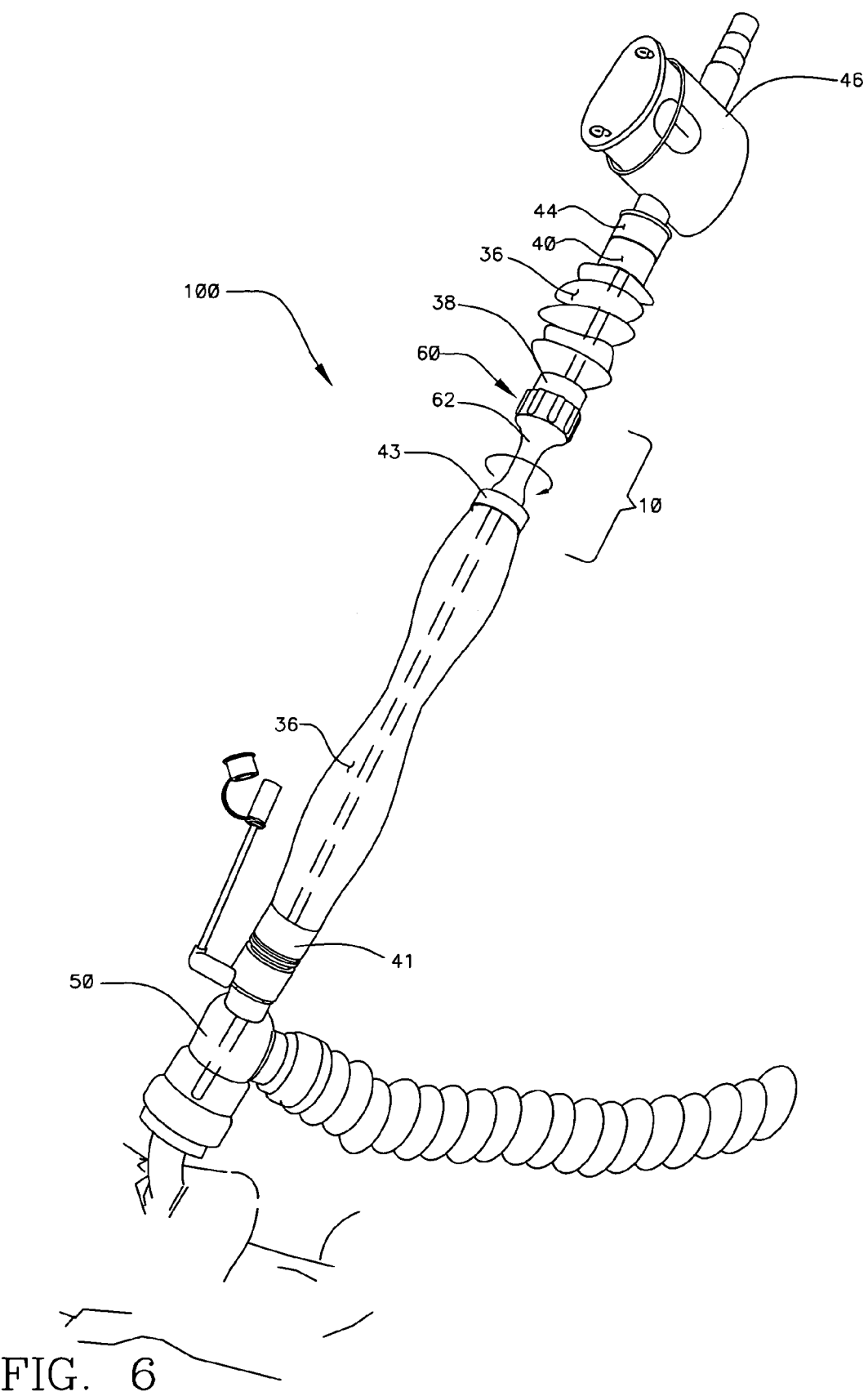
FIG. 6 is a perspective view of the clamping assembly positioned about a catheter assembly such that distal movement of the tube of the catheter assembly may be limited.

An aspect of a clamping assembly according to the present invention is illustrated generally at 10 in the figures. The assembly 10 is particularly configured for use in a respiratory care assembly which is adapted to insert a medical treatment device, such as a catheter tube, into a patient's respiratory system through an artificial airway. In some instances, an airway connector, such as the manifold 50 shown in FIGS. 5 and 6 is connected to the patient's artificial airway.

Figure 2:
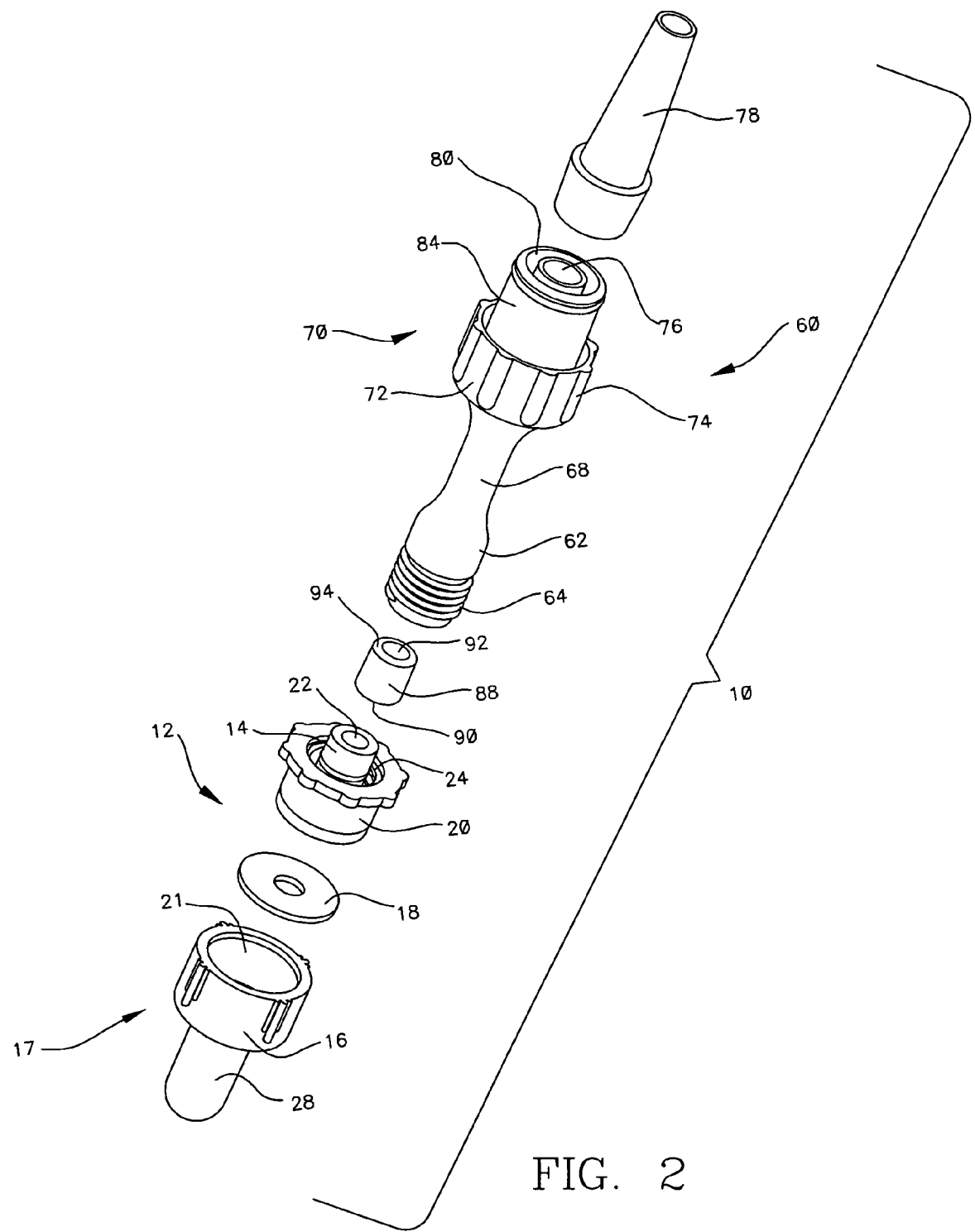
FIG. 2 is an alternate exploded component view of the clamping assembly.

Referring to FIGS. 1 and 2 in particular, the clamping assembly 10 according to the present invention includes a first or distal member 12, and a second or proximal member 60. In the aspect illustrated in FIGS. 1 and 2, the first or distal member 12 includes an end portion 20 and an optional attachment mechanism 17 which may be used to facilitate attachment of the distal member to a medical treatment device or artificial airway or the like. Depending on the medical treatment device or medical treatment device assembly used therewith, the attachment mechanism 17 may take many shapes, for example, the attachment mechanism 17 may be as illustrated in FIGS. 1 and 2 or it may take the form of a snap ring or compression fit ring 43 as suggested in FIGS. 3-6 and similar to rings 38 and 40 (FIGS. 3-6). The attachment mechanism 17 may include, in selected aspects, a base 16, a seal 18, a seal retainer (FIG. 3) and/or a connecting member 28. In certain aspects of the present invention, the connecting member 28 and the base 16 may be formed as a single piece such as, for example, by injection molding.

In the aspect depicted in FIGS. 1 and 2, the base 16 includes an internal recess 21. The distal portion of the end portion 20 may be inserted into the recess 21 of the base 16. A seal 18 having a hole 19 may be disposed between the end portion 20 and the base 16 within the recess 21. The seal serves to scrape mucous and other secretions from the surface of a catheter tube 34 withdrawn therethrough, as explained in greater detail below. The need or desire to include a seal at the distal end of the first member 12 will depend in part on the type of procedure to be performed as well as the other components of the medical treatment device and the position of the clamping assembly relative to those other components of the medical treatment device assembly. The end portion 20 may also be otherwise engaged to the base 16.

The end portion 20 may also include, in particular embodiments, a threaded inner diameter portion 24 which is best shown in FIG. 2.

As shown in FIGS. 1 and 2, the first or distal member 12 also includes a channel 22 which extends axially through the attachment mechanism 17, the hole 19 and the end portion 20.

The proximal member 60, as shown in FIGS. 1 and 2, includes an elongated base member 62 which includes a restraining recess 66, a threaded outer diameter portion 64, a grip enhancing member 70, an elongated shaft 68 and a medical device connector 82. The restraining recess 66 is defined in the distal end of the base member 62. The threaded outer diameter portion 64 is adapted to engage the threaded inner diameter portion 24 of the distal member 12.

To aid the clinician in manipulation of the proximal or second member 60, it may be desired to provide a grip enhancing member 70 on an exterior surface of the proximal member 60. For example, in FIG. 1, the grip enhancing member 70 includes a radially extending gripping ring 72 which includes a plurality of protrusions 74 disposed therearound. The outermost diameter of the ring 72 may be selected so that the gripping ring does not interfere with the operation of the medical device by the clinician. The gripping ring 72 may be variously positioned on the clamping assembly 10. For example, an elongated shaft 68 may be disposed between the threaded distal end 64 and the gripping ring 72. By moving the gripping ring 72 away from patient's artificial airway and closer to the clinician, the clinician is provided with adequate space to actuate and adjust the clamping assembly 10, if necessary.

Depending on the medical treatment device a particular clamping assembly 10 is intended for use with, the proximal member 60 may also include a medical device connector 82, for permanently or removably connecting the proximal member 60 to any manner of medical treatment device. When present, the type and/or size and shape of a medical device connector 82 may be varied to accommodate a particular medical treatment device or component thereof as well as the location of the clamping assembly 10 relative to the medical treatment device. For example, as noted above, the clamping assembly 10 may be assembled as part of a medical treatment device such as a catheter assembly 30 (FIGS. 3-6) or the clamping assembly 10 may be an independent component. In the aspect illustrated in the figures, clamping assembly 10 is permanently attached to the catheter assembly 30 and more particularly to or between portions of the protective sleeve or sheath 36 of the catheter assembly 30. It will be appreciated that the medical device connector 82 is not necessary and is optional as the clamping assembly 10 may be glued or otherwise secured (i.e., clamped, compression fit, etc.) to the respectively corresponding portions of the sheath 36.

It should be appreciated that the first and second members 12, 60 are not limited by their shape and configuration; however, certain embodiments may impose restrictions on the shape and configuration of certain components.

The first and second members 12 and 60, respectively, are axially aligned so that their respective axial channels 22 and 76 form a continuous axially extending channel through the aligned components. This channel is appropriately sized to receive a medical treatment device, such as a catheter tube. In an unclamped configuration of the clamping assembly 10, the catheter tube or other treatment device is able to axially slide through the assembly 10 and into the respiratory tract of an intubated patient.

For purposes of discussion, a catheter will be used as an exemplary medical treatment device. It should, however, be appreciated, that the present invention is not limited to use with a catheter, but may be used in any application wherein it is desired to axially position and then further limit insertion or distal advancement of a medical treatment device relative to the patient's respiratory tract.

The distal and proximal members 12, 60 are configured so that there may be movement between the members. In the illustrated aspect, this movement is in an axial direction and may be accomplished by threaded engagement between the members. While desirable for both the distal and proximal members 12, 60 to be capable of rotational movement relative to one another so as to facilitate such a threaded engagement, it will be appreciated that either member may be fixed such that only one of the members rotates relative to the other. As described elsewhere herein, it will also be appreciated that other non-rotational ways of relative axial movement between the distal and proximal members is also contemplated.

Referring particularly to FIGS. 1 and 2, a clamping member is positioned between the first or distal member 12 and the second or proximal member 60. The clamping member is actuated by the relative movement between the distal and proximal members 12 and 60, respectively. For example, in the illustrated aspect the clamping member includes a compressible annular sleeve 88 having a channel 94 defined therethrough. The channel 94 is in axial alignment with the channels 22 and 76 that are defined through the distal and proximal members 12 and 60, respectively, and thus forms at least a portion of the axial channel through which the catheter tube passes. The annular sleeve 88 has an unclamped configuration wherein the catheter tube is freely slidable through the assembly 10, and a clamping position wherein the annular sleeve 88 compresses or deforms upon and restricts relative axial movement of the catheter tube 34 through the assembly 10, as described in greater detail below.

The compressible annular sleeve 88 is disposed so that its proximal end 92 is contacted by the second or proximal member 60 and its distal end 90 is contacted by the first or distal member 12. For example, referring to FIGS. 1 and 2, the annular sleeve 88 is disposed in a closed-end recess 66 defined in the distal end of the second or proximal member 60. This recess has a fixed diameter slightly greater than the outer diameter of the sleeve 88. Referring to FIG. 2, an axial protrusion 14 of the first or distal member 12 abuts against the distal end 90 of the annular sleeve 88. Upon rotation of the second or proximal member 60 in a tightening direction, the second or proximal member 60 is drawn towards stationary first or distal member 12. This results in axial compression of the annular sleeve 88 within the recess 66. This axial compression results in a radial expansion of the annular sleeve. However, because the sleeve is restrained or restricted within the fixed diameter recess 66, the radial expansion is directed radially inward causing the inner diameter of the annular sleeve 88 to compress or reduce. This reduction of the inner diameter results in the annular sleeve 88 securely clamping upon a catheter tube disposed therethrough. The clamping assembly is designed such that the annular sleeve 88 clamps upon the catheter tube 34 so as to restrict axial movement of the tube relative to the annular sleeve 88 and clamping assembly 10, yet still allows for fluid flow (e.g., suctioning, etc.) therethrough.

Thus, in an unclamped configuration of the assembly 10, a clinician can easily slide a catheter tube or like device through the assembly 10 and into the patient's respiratory tract to a desired axial location. In order to lock the catheter tube at this position relative to the clamping assembly 10 shown in the figures, the clinician simply rotates the second or proximal member 60 in a tightening direction causing the annular sleeve 88 to clamp upon the catheter tube 34. The catheter tube is restricted from further axial movement within the assembly 10 until the clinician rotates the second or proximal member 60 in the opposite direction. At this point (i.e., after the clinician rotates the second or proximal member 60 such that the clamping assembly 10 is in an unclamped configuration), the catheter tube 34 can be freely moved through the clamping assembly 10 and withdrawn from the patient. As will be noted in more detail below, the catheter tube 34 may be at least partially withdrawn from the patient at any time even if the clamping assembly 10 is in a clamped configuration; however, distal axial movement of the tube relative to the patient beyond the point or depth corresponding to the position at which the clamping assembly 10 was placed in a clamped configuration may not be possible when the assembly 10 is in a clamped configuration. That is, a stopping member or blocking member is present and restricts movement of the clamping assembly 10 in an axially distal direction when the blocking or stopping member comes in contact with the clamping assembly 10. The effect of the contact between the blocking or stopping member and clamping assembly 10 when the clamping member is in the clamped configuration is that the medical treatment device is only slidable in the distal direction until the clamping assembly 10 contacts the blocking member, thereby limiting the depth of insertion to which the medical treatment device may be inserted in the clamped configuration.

The present invention contemplates that while there may be direct physical contact between the clamping assembly and the blocking member, there are a number of instances in which actual physical contact between the two components does not occur but which are intended to fall within the scope of the invention. For example, where contact between the clamping assembly and the blocking member is mentioned, it is also contemplated to include situations such as those wherein a portion of a sheath or the like is positioned between the blocking member and the clamping assembly and prevents actual physical contact but in which the clamping assembly and the blocking member would contact each other in the absence of such a sheath or the like. That is, for example, where a fold or the like in a protective sheath comes between the assembly and the blocking member and contact would occur but for the sheath. Alternatively, where the sheath bunches and prevents or restricts distal movement of the clamping assembly such that the clamping assembly and the blocking member are unable to come into contact with each other. In either instance, as well as in other similar situations, it shall for purposes of this disclosure be deemed that the clamping assembly and blocking member have come in contact with each other.

It will be appreciated that the clamping assembly 10 may have at its distal end a extension or the like (not shown) which extends from the distal end of the clamping assembly in a distal direction and which is intended to contact the blocking member and thereby restrict further distal movement of the clamping assembly. The extension may be integrally attached or separately mounted to the distal end of the clamping assembly and may be designed to fit within or about a sheath of a medical treatment device, where present. In one aspect, it is contemplated the extension be of such dimensions that it allows a medical treatment device to pass through the extension yet be enclosed within a sheath 36. In another aspect the extension may be such that it is positioned outside of a sheath 36, where such a sheath is present. It is further contemplated that the extension may be cylindrical in shape so as to be able to surround a medical treatment device. Where the extension is cylindrical in shape and is to be positioned inside of a sheath, it is desirable for the extension to have an inner diameter slightly larger than the outer diameter of the medical treatment device. In those instances where the extension is to be outside of the sheath, it is desirable for the extension to be dimensioned such that it does not interfere with the ability to advance or retract the sheath nor interfere with the bunching of the sheath. Whether inside or outside the sheath, it is contemplated the extension may take any other suitable configuration. That is, the extension need not surround the medical treatment device, rather, it could, for example, extend on one or more sides of the medical treatment device or only surround a portion of the medical treatment device.

Figure 3:
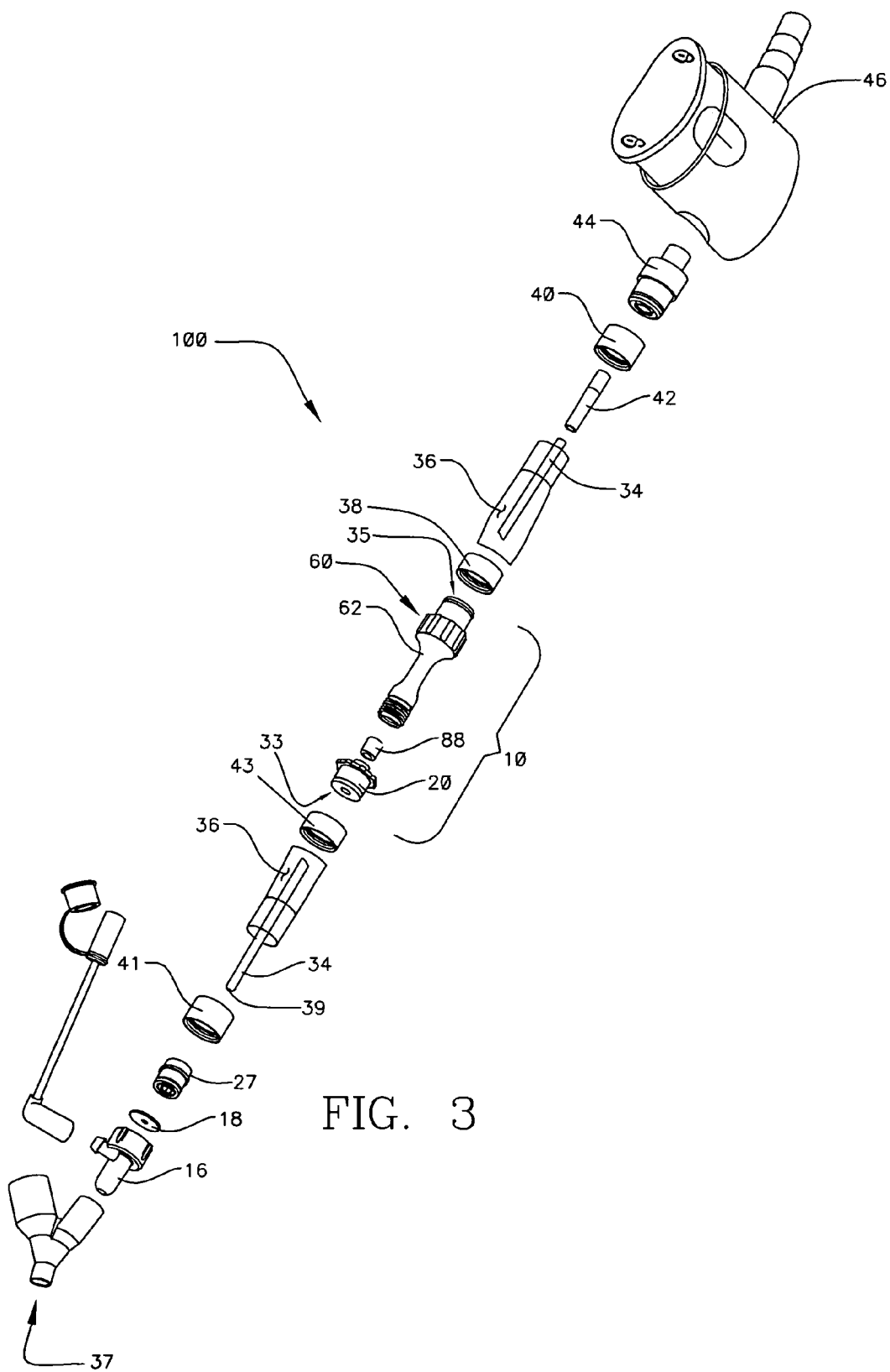
FIG. 3 is a perspective exploded view of the clamping assembly and a catheter assembly.
Figure 4:
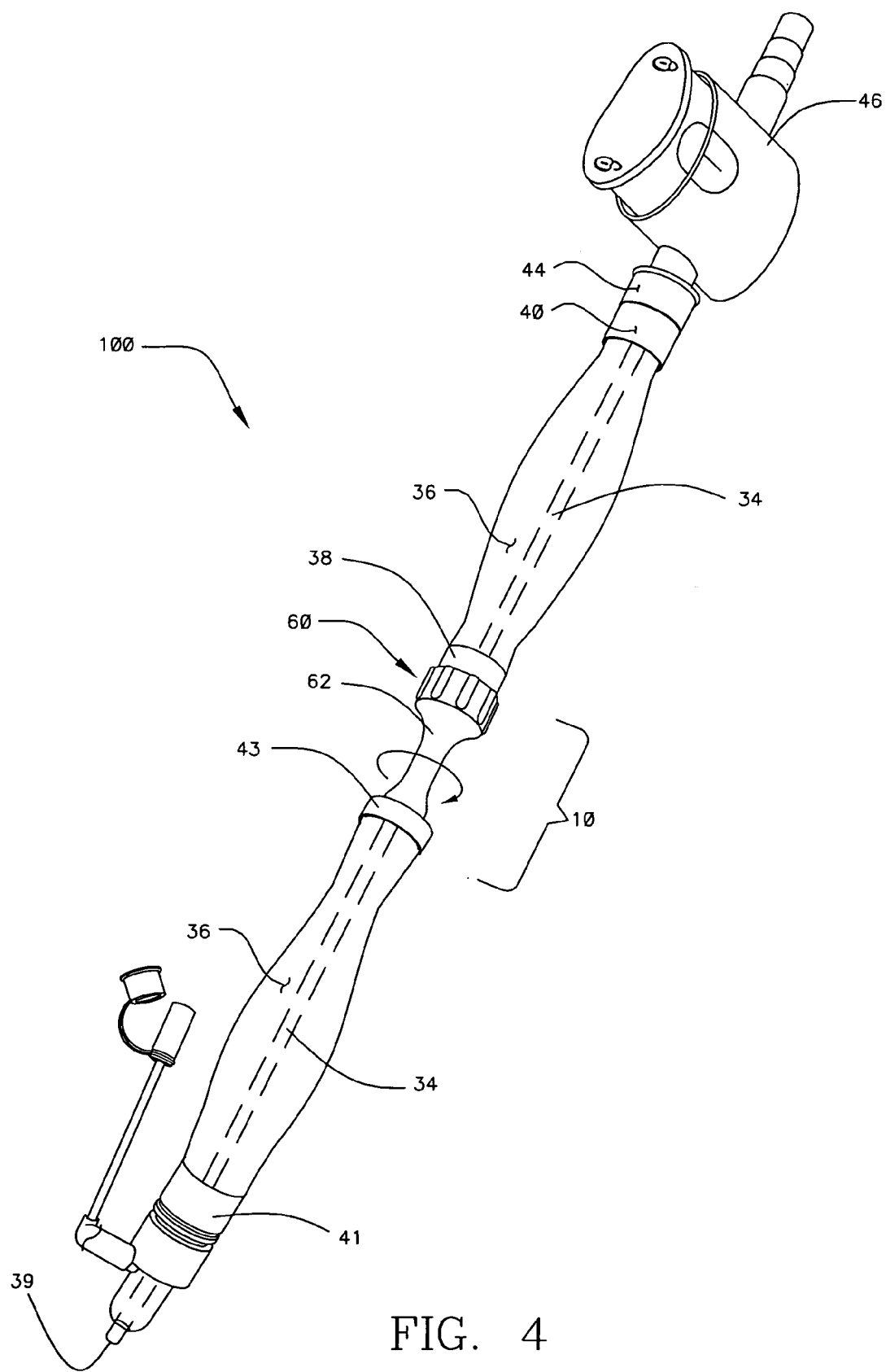
FIG. 4 is a perspective view of the assembly illustrated in FIG. 3.

FIGS. 3 through 6 illustrate a representative respiratory care assembly 100 incorporating the novel clamping assembly 10 discussed above. Referring to FIGS. 3 and 4, the treatment device is illustrated as a catheter assembly 30 having a catheter tube 34 slidable within a sheath 36. As illustrated the sheath 36 is shown in two sections, one extending from the proximal end of the catheter 30 to the proximal end 35 of the clamping assembly 10, the other section of the sheath 36 extending from the distal end 33 of the clamping assembly 10 towards the distal end 37 of the catheter assembly 30. One end of each section of the sheath 36 may be secured to the clamping assembly 10 so as to prevent leakage of fluids between the sheath 36 and the clamping assembly 10. The connections may be made by any suitable manner, for example by gluing or press-fitting. For example, the end of the sheath 36 which is to be secured to the proximal end 35 of the clamping assembly 10 may be placed around the cylindrical portion 84 (FIGS. 1 and 2) of the proximal member base 62 and the distal ring 38 may be press or snap-fit onto the cylindrical portion 84 to secure the distal end of the proximal portion of the sheath 36 to the clamping assembly 10. A proximal ring 40 may be press or snap fit onto an adaptor 44 and secures the proximal end of the sheath 36 relative to the adaptor 44. A bushing 42 may be disposed around the proximal end of the catheter tube 34. The adaptor 44, in turn, may be connected to or formed integral with a proximal connector 46. The connector 46, in turn, may be connected to an air or oxygen source, suction source, lavage solution source, etc., depending on the particular medical procedure to be performed. For example, the catheter assembly 30 illustrated in FIGS. 3 and 4 is particularly suited for a secretion aspiration procedure to remove secretions from a patient's lungs while the patient is on a ventilator. The connector 46 is connectable with a vacuum source for suctioning mucous, secretions, and other fluids through the catheter tube 34. In use, the clinician may advance the distal end 39 of the catheter tube 34 through the clamping assembly 10 until it is at the desired position at the carina of the lung and then may secure the catheter tube in position relative to the clamping assembly 10 by actuating the clamping assembly 10 as described above such that no further distal movement of the catheter tube 34 is possible. Suction may then be applied to the catheter to remove the mucous, secretions, and other fluids from the patient's lungs.

Once the desired suctioning or aspiration has occurred the catheter tube 34 may be moved axially in a proximal direction. As the clamping assembly 10 has not been released from the catheter tube 34, the clamping assembly 10 is still clamped upon the catheter tube 34 and will move proximally as the catheter tube moves proximally. Proximal axial movement of the catheter tube may be somewhat limited by the amount of material comprising sheath 36 which is present distal to the clamping assembly 10. That is, while the catheter tube 34 and clamping assembly 10 are not limited in concept as to the axial distance they may move in the proximal direction, their movement may be restricted by the length of the material comprising sheath 36 which is positioned distally of the assembly 10, for as the assembly 10 moves proximally the material of sheath 36 distal the clamping assembly 10 will begin to straighten out and possibly stretch. However, once the sheath 36 has reached its maximum length (based on the amount of sheath present as opposed to sheath characteristics), the assembly may not be permitted to move further in a proximal axial direction. Thus, there may be instances where a complete withdrawal of the catheter tube 34 from the artificial airway of a patient may not occur.

In those situations in which only partial withdrawal occurs care should be taken to ensure that any of the medical treatment device which is not fully withdrawn does not interfere with the patient's ability to breathe. If complete withdrawal is necessary a medical treatment device such that the clamping assembly 10 is positioned in manufacture farther up the sheath to minimize partial withdrawal may be used. That is, the more proximal the positioning of the clamping assembly 10 in the sheath 36 of the medical treatment device the less likely partial withdrawal will be an issue.

Turning now to FIGS. 5 and 6, it may be seen that upon reinsertion or reintroduction of the catheter tube 34 into the patient's airway, the distal end 33 (FIG. 3) of the clamping assembly 10 will contact a blocking or stopping member (in this case, ring 41) of the catheter assembly 30 if inserted far enough. As the catheter tube 34 is restricted from further axial movement relative to the clamping assembly 10 while the assembly is in a clamped configuration, once the distal end 33 of the clamping assembly 10 contacts the blocking or stopping member of the catheter assembly 30, the catheter tube 34 will be restricted from further distal movement. The restriction of further distal movement within the patient's respiratory system will restrict overinsertion of the catheter tube 34 provided that the clamping assembly 10 was properly positioned on or about the tube 34 the first time.

While the clamping assembly 10 will generally be operated to a clamped configuration once the medical treatment device has been positioned within the patient's respiratory system or artificial airway as desired, it will be appreciated that a medical treatment device may be advanced within the clamping assembly 10 to a known or desired position and that the clamping assembly 10 may be operated to a clamped configuration prior to insertion of the medical treatment device into a patient, artificial airway, or the like. Fixing the medical treatment device prior to insertion into a patient is generally recommended only where over insertion is not a concern or where the preset depth is known to be less than that which would result in overinsertion.

It will also be appreciated that while the blocking member may be part of, located on, or attached to the medical treatment device, the blocking member may also be independent thereof. In certain instances a patient, and more particularly, a surface thereof may be or act as the blocking member.

So long as the clamping assembly 10 remains secured to the catheter tube 34, repeated insertions of the catheter tube 34 may be made into the patient's respiratory system and/or artificial airway without having to determine or redetermine the proper depth of insertion of the tube. The present invention will thus allow for the ability of shorter procedure times without an increase in the risk of causing damage to the patient's respiratory system and in fact should significantly reduce the number of injuries to patients as a result of overinsertions of catheters, especially on the second or subsequent uses of a catheter on a patient.

The present invention is also directed to a method of providing a system for limiting the depth of insertion or distal advancement of a medical treatment device to a clinician. The method may include the steps of providing a clamping assembly, the clamping assembly having at least a clamped configuration and an unclamped configuration; providing a medical treatment device, at least a portion thereof being configured to pass through the clamping assembly; and providing information to the clinician regarding: sliding at least a portion of the medical treatment device through the clamping assembly, and operating the clamping assembly such that axial movement of the medical treatment device relative to the clamping assembly is restricted; thereby enabling the clinician to limit the depth of insertion or distal advancement of a medical treatment device into a patient. It is contemplated that any suitable clamping assembly may be used as may any suitable medical treatment device. Suitable clamping assemblies include, for example, those discussed in detail above, including one having: a first distal member and a second proximal member, at least one of said first and second members moveable relative to said other respective member; an axial channel defined through said first and second members for sliding receipt of a medical treatment device therethrough; a clamping member disposed in-line with said first and second members, said clamping member having an unclamped configuration wherein said catheter tube is slidable through said channel, and a clamping position wherein said clamping member clamps upon and restricts axial movement of said catheter tube relative to said channel, at least one of said first and second members being movable to change said clamping member from said unclamped configuration to said clamping configuration moving to change said clamping member from said unclamped configuration to said clamping position, wherein said clamping member is positioned proximally to said first distal member; wherein said clamping member is actuated by relative movement between said first and second members; wherein said clamping member is restricted from moving in an axially distal direction by a blocking member; and wherein when said clamping member is in said clamped configuration said medical treatment device is only slidable in a distal direction until the clamping member contacts the blocking member, thereby limiting the depth of insertion to which the medical treatment device may be inserted in the clamped configuration.

It is also contemplated that a kit for use in the method of providing a system could include at least one clamping assembly, at least one medical treatment device, a package containing the clamping assembly and medical treatment device, and indicia on the package to inform a clinician how said clamping assembly is to be used. It will be further appreciated that the indicia informing a clinician how the clamping assembly is to be used may be contained within the package rather than on the package. It is further contemplated that a kit may also include a variety of other accessories including, for example, gloves, pads, wipes, drapes, iodine, sutures, various adaptors for use with the clamping assembly or medical treatment device(s), etc.

The present invention has a number of benefits over existing products, more specifically, the present invention provides a clamping mechanism that need not be fixed at the distal end of a catheter or medical treatment device. The present invention also provides a clamping mechanism that is readily accessible to a clinician and is not covered by a sheath or the like thereby facilitating access and use.

It should be appreciated that the arrangement of FIGS. 5 and 6 is presented for illustrative purposes only and that the present invention is not limited to any particular type of system or device for connection to the patient's artificial airway.

It may be desired to form some or all of the components of the present invention out of clear or translucent materials such that a visual inspection of the components or the ongoing medical procedure is possible. For example, this would allow the clinician to monitor the color and consistency of mucous and secretions in an aspiration procedure.

It should also be understood that the components described herein may be formed of a variety of materials and from a variety of manufacturing processes. In some aspects of the present invention, the components of the present invention may be injection molded from a medical grade synthetic resinous material, such as an acrylic, flexible PVCS, modified polypropylene, or similar substances.

It should be appreciated by those skilled in the art that various modifications and variations can be made in the present invention without departing from the scope and spirit of the invention. It is intended that the present invention include such modifications and variations as come within the scope of the appended claims and their equivalents.

What is claimed is:

1. A clamping assembly for use with a respiratory care medical treatment device, said assembly comprising:
   a first member;
   a second member connected to said first member, said first member and said second member being axially movable relative to each other, at least one of said members being at least partially rotatable;
   a channel defined through said second and first members, said channel configured for receipt of at least a portion of a medical treatment device passing therethrough;
   a clamping member operatively configured between said second and first members and defining at least a portion of said channel, said clamping member having an unclamped configuration wherein said medical treatment device is slidable through said clamping member and channel, and a clamping configuration wherein said clamping member clamps upon and restricts axial movement of said medical treatment device through said channel, at least one of said members being capable of rotating to engage and move said clamping member from said unclamped configuration to said clamping configuration, wherein said clamping member is positioned proximally to said first member;
   wherein said clamping member is actuated by axial movement between said second and first members; and
   wherein when said clamping member is in said clamped configuration said medical treatment device is only slidable in a distal direction until a first end of the clamping assembly contacts a stopping member.

2. The assembly as in claim 1, wherein the clamping assembly is positioned between portions of a sheath of the said medical treatment device.

3. The assembly as in claim 1, wherein the stopping member is part of the medical treatment device.

4. The assembly as in claim 1, wherein said second member and said first member are threadedly engaged.

5. The assembly as in claim 4, wherein said second member is threadedly engaged with end axially movable relative to said first member, said clamping device comprising a compressible annular sleeve having an inner diameter that reduces upon said annular sleeve being compressed by relative axial advancement of said second member towards said first member thereby causing said annular sleeve to clamp upon the medical treatment device disposed therethrough.

6. The assembly as in claim 1, wherein said clamping device comprises a compressible annular sleeve having opposite ends in contact with said second end first members respectively, said annular sleeve disposed within a fixed diameter axially extending recess defined by one of said second and first members such that relative axial movement between said second and first members causes axial compression of said annual sleeve within said recess.

7. The assembly as in claim 6, wherein said second member is threadedly engaged with and axially advanceable relative to said first member, said second member defining said axially extending recess and said first member comprising an axially extending protrusion extending into said recess and in contact with a distal end of said annular sleeve.

8. The assembly as in claim 1, wherein at least one of said first and said second members further comprising a gripping member axially spaced from a point of connection between said first and second members.

9. A clamping assembly for use with a respiratory care medical treatment device, said assembly comprising:
   a first distal member and a second proximal member, at least one of said first and second members moveable relative to said other respective member;
   an axial channel defined through said first and second members for sliding receipt of a respiratory care catheter tube therethrough;
   a clamping member disposed in-line with said first and second members, said clamping member having an unclamped configuration wherein said catheter tube is slidable through said channel, and a clamping position wherein said clamping member clamps upon and restricts axial movement of said catheter tube relative to said channel, at least one of said first and second members being capable of moving to change said clamping member from said unclamped configuration to said clamping position, wherein said clamping member is positioned proximally to said first distal member;

wherein said clamping member is actuated by relative movement between said first and second members;

wherein said clamping member is restricted from moving in an axially distal direction by a blocking member; and wherein when said clamping member is in said clamped configuration said medical treatment device is only slidable in a distal direction until the clamping member contacts the blocking member, thereby limiting the depth of insertion to which the medical treatment device may be inserted in the clamped configuration.

10. The assembly as in claim 9, wherein the blocking member is part of the medical treatment device.

11. The assembly as in claim 10, wherein the medical treatment device is catheter assembly.

12. The assembly as in claim 9, wherein said clamping member comprises a compressible annular sleeve member having opposite axial ends in contact with said first and second members respectively, said annular sleeve member defining at least a portion of said axial channel; and wherein upon relative axial movement of said first and second members, said annular sleeve is compressed axially and radially inwardly and thereby clamps upon said catheter tube disposed therethrough, and upon opposite axial movement of first and second members, said annular sleeve releases said catheter tube.

13. A respiratory care assembly, comprising:
a catheter assembly having a catheter tube configured for insertion through a patient's artificial airway;
a clamping assembly for connecting said catheter assembly to the patient's artificial airway, said clamping assembly further comprising:
a proximal member axially aligned with a distal member, said proximal member and said distal member being movable relative to each other;
a channel defined through said proximal and distal members, said catheter tube slidable through said channel for insertion into the patients artificial airway;
a clamping member disposed in-line with said proximal and distal members, said clamping member hiving an unclamped configuration wherein said catheter tube is slidable through said channel, and a clamping position wherein said clamping member clamps upon and restricts axial movement of said catheter tube relative to said channel, at least one of said proximal and distal members being capable of moving to change said clamping member from said unclamped configuration to said clamping position, wherein said clamping member is positioned proximally to said distal member;
wherein said clamping member is actuated by movement between said proximal and distal members; and
wherein said clamping member is restricted from moving in an axially distal direction by a blocking member; and
wherein when said clamping member is in said clamped configuration said medical treatment device is only slidable in the distal direction until the clamping member contacts the blocking member, thereby limiting the extent to which the catheter tube may be distally advanced in the clamped configuration.

14. The respiratory care assembly as in claim 13, wherein said proximal and distal members are axially moveable relative to each other and said clamping member comprises a compressible annular sleeve member having opposite axial ends in contact with said proximal and distal members respectively, said annular sleeve member defining at least a portion of said channel; and wherein upon relative axial movement of said proximal and distal members, said annular sleeve is compressed axially and radially inwardly and thereby clamps upon said catheter tube disposed therethrough.

15. The respiratory care assembly as in claim 14, wherein said annular sleeve is disposed within a fixed diameter axially extending recess defined by one of said proximal and distal members.

16. The respiratory care assembly as in claim 13, wherein said proximal and distal members are threadedly engaged.

17. A method for limiting the depth of insertion or distal advancement of a medical treatment device, the method comprising:
providing a clamping assembly, the clamping assembly having at least a clamped configuration and an unclamped configuration;
providing a medical treatment device, at least a portion thereof being configured to pass through the clamping assembly;
sliding at least a portion of the medical treatment device through the clamping assembly;
operating the clamping assembly such that axial movement of the medical treatment device relative to the clamping assembly is restricted; wherein after operating the clamping assembly so as to restrict axial movement of the medical treatment device relative to the clamping assembly, the medical treatment device is slidable in a distal or proximal axial direction but only in the distal direction until the clamping assembly contacts a blocking member.

18. A method for limiting the depth of insertion or distal advancement of a medical treatment device, the method comprising:
providing a clamping assembly, the clamping assembly having at least a clamped configuration and an unclamped configuration;
providing a medical treatment device, at least a portion thereof being configured to pass through the clamping assembly;
sliding at least a portion of the medical treatment device through the clamping assembly;
operating the clamping assembly such that axial movement of the medical treatment device relative to the clamping assembly is restricted wherein the clamping assembly is a clamping assembly for use with a respiratory care medical treatment device, said assembly comprising:
a first distal member and a second proximal member, at least one of said first and second members moveable relative to said other respective member;
an axial channel defined through said first and second members for sliding receipt of a respiratory care catheter tube therethrough;
a clamping member disposed in-line with said first and second members, said clamping member having an unclamped configuration wherein said catheter tube is slidable through said channel, and a clamping position wherein said clamping member clamps upon and restricts axial movement of said catheter tube relative to said channel, at least one of said first and second members being movable to change said clamping member from said unclamped configuration to said clamping configuration moving to change said clamping member from said unclamped configuration to said clamping position, wherein said clamping member is positioned proximally to said first distal member;

wherein said clamping member is actuated by relative movement between said first and second members;

wherein said clamping member is restricted from moving in an axially distal direction by a blocking member; and wherein when said clamping member is in said clamped configuration said medical treatment device is only slidable in a distal direction until the clamping member contacts the blocking member thereby limiting the depth of insertion to which the medical treatment device may be inserted in the clamped configuration.

* * * * *